United States Patent [19]

Pfleuger

[11] Patent Number: 5,462,737
[45] Date of Patent: Oct. 31, 1995

[54] CHEMICAL COMPOSITION FOR LIPSTICK SEALANT

[76] Inventor: D. Russell Pfleuger, 3 Cavalier, Laguna Niguel, Calif. 92677

[21] Appl. No.: 247,713

[22] Filed: May 23, 1994

[51] Int. Cl.$^6$ ................................................. A61K 7/025
[52] U.S. Cl. .............................. 424/401; 424/63; 424/64; 514/781; 514/783
[58] Field of Search ................................ 424/64, 63, 401; 106/215, 237

[56] References Cited

U.S. PATENT DOCUMENTS

| | | | |
|---|---|---|---|
| 2,230,063 | 1/1941 | Klimist | 167/85 |
| 2,936,245 | 5/1960 | Osipow | 106/189 |
| 3,403,040 | 9/1968 | Osipow | 106/173 |

*Primary Examiner*—Thurman K. Page
*Assistant Examiner*—Sharon Howard
*Attorney, Agent, or Firm*—Cornelius J. Husar

[57] ABSTRACT

A liquid sealant composition is provided which forms a transparent, water-insoluble, flexible film over lipstick. It prevents lipstick from coming off when the lips come in contact objects such as with cups, drinking glasses, clothing, and food. The composition comprises ethyl cellulose, essential oils, and ethanol. Unlike such compositions known to the prior art, it causes no stinging or burning sensation on the lips after application, it has no irritating odor, and it uses no environmentally objectionable volatile chlorofluorocarbons.

8 Claims, No Drawings

CHEMICAL COMPOSITION FOR LIPSTICK SEALANT

BACKGROUND OF THE INVENTION

1. Field of the Invention

This invention relates to a liquid sealant composition. More particularly, it relates to a lipstick sealant composition which is used to form a transparent, flexible, water-insoluble film over lipstick. It prevents lipstick from coming off when the lips come in contact with objects such as cups, drinking glasses, clothing, and food.

2. Prior Art

Lip rouge, lipsticks, and coatings to be applied over lipstick have been known for many years. Lipsticks are made of fatty and waxy materials, dyes and/or pigments, and fragrances. An objectionable feature of lipstick is the fact that it is readily transferred from the lips of the wearer to any objects that come in contact with the lips. The inclusion in the lipstick formulation of compositions forming a moisture-proof, smear-proof film, and the separate application over the lipstick of compositions forming such a film, has solved this problem.

U.S. Pat. No. 2,230,063 discloses a formulation including dyes and pigments in a mixture of ethyl cellulose, ethanol, acetone, petroleum ether, and a plasticizer. Upon evaporation of the ethanol, acetone, and petroleum ether, a water insoluble film is left on the lips which does not run and smear. The principal objection to the formulation of this invention is the fact that the ethanol and petroleum ether cause an unpleasant stinging sensation on the lips while they evaporate. Additionally, the petroleum ether emits an unpleasant odor which is difficult to mask and it imparts an unfamiliar taste.

U.S. Pat. Nos. 2,936,245 and 3,403,040 seek to overcome the problem of the stinging sensation on the lips by providing a coating composition, which is applied over lipstick, which includes volatile chlorofluorocarbons, especially chlorofluorocarbons 113 (1,2,2-trifluoro-1,1,2-trichloro ethane). The principal objection to the use of chlorofluorocarbons is the fact that these substances have been recognized in recent years to contribute to global warming and to upper-atmospheric ozone depletion. For environmental reasons, the use of chlorofluorocarbons will be reduced or eliminated altogether worldwide in coming years.

Although fully halogenated halocarbons are considered to be relatively nontoxic, their inhalation during the application of these formulations to the lips is almost inevitable and may be considered to pose a modest health risk to the user. Chlorofluorocarbons also emit an unpleasant odor which is difficult to mask and impart an unfamiliar taste.

SUMMARY OF THE INVENTION

The present invention overcomes the objections to the lip rouge and sealant compositions of the prior art discussed above by its unique composition. The composition of the present invention is intended to be applied over lipstick and comprises ethyl cellulose, 5–10 percent; essential oils, 0–4 percent, the remainder being ethanol. It provides, upon ultra rapid evaporation of the ethanol, a transparent, flexible, water-insoluble film eliminating the smudging, smearing, and running of lipstick. It causes no unpleasant burning or stinging sensation on the lips during the short time needed for evaporation of the ethanol. It employs no potentially harmful chlorofluorocarbons. The odor of ethanol is masked by the essential oils, and the taste is familiar and not unpleasant.

OBJECTS OF THE INVENTION

An object of this invention is to provide a lipstick sealant having an evaporation of less than thirty seconds when applied to the lips of the wearer.

A further object of the invention is to provide a lipstick sealant which has a film durability in excess of known sealants.

Yet another object of the invention is to provide a lipstick sealant having a pleasant aroma with a minimum trace of solvent odor.

A still further object of the invention is to provide a lipstick sealant which will not cause any stinging sensation when applied to normal (nonchapped) lips.

Another object of the invention is to provide a lipstick sealant that creates a film which can withstand flexing of at least 180 degrees without cracking.

Yet another object of the invention is to provide a lipstick sealant that creates a film which imparts no detectable stickiness when the film is fully set.

A further object of the invention is to provide a lipstick sealant that provides a protective film using ingredients which are considered safe for regular skin contact, and environmentally safe.

These and other objects of the instant invention will become more apparent after a reading of the detailed description of the invention hereinafter.

DETAILED DESCRIPTION OF THE INVENTION

The composition of the lipstick sealant of this invention for forming a water-insoluble, transparent, flexible film over lipstick contains 5%–10% by weight of ethyl cellulose, 0%–4% by weight of essential oils, the remainder being 200-proof (anhydrous) ethanol. The preferred range of ethyl cellulose content is 6%–8% by weight.

The key to the success of the formulation of this invention in avoiding the burning sensation on the lips during the evaporation of the ethanol lies in its composition. The prior art suggests that the percentage of ethyl cellulose should not exceed 5%. It has now been demonstrated, however, that the optimum range of ethyl cellulose content is 5%–10%, preferably 6%–8%. The higher ethyl cellulose content produces a film which is substantially more durable and less sticky.

The ethyl cellulose should have an ethoxyl content of 48% to 49.5%, and a substitution of ethoxyl groups of 2.41 to 2.51 per anhydroglucose unit. The viscosity of a test solution of ethyl cellulose, as determined by ASTM D-419, containing 5% by weight of ethyl cellulose in a mixture of 80% toluene and 20% ethanol by volume, should be 8 to 11 centipoises when measured at 25° C.

In addition, it has been found that the essential oil content of the formulation should not exceed 4% as a drop-off in the durability of the sealant film is noted at higher concentrations of essential oils. As the percentage of essential oil approaches 0 percent, the ethanol odor becomes pugnacious, the film becomes less flexible, and there is an increase in the burning sensation when the formulation is applied to the lips. The essential oils that may be included in the formulation include cocunut oil, vanilla oil, bergamot oil, and lavender oil.

The composition of this invention, when applied to the lips to form a water-insoluble, transparent, flexible film, dries in approximately 30 seconds and causes no stinging or burning sensation on unchapped lips. It prevents the transfer of lipstick to objects coming in contact with the lips.

In the foregoing, a specific set of details as to the coating composition of this invention has been provided. It will be understood that many changes can be made in these details without departing from the spirit of the invention or the scope of the following claims.

Having thus described my invention, I claim:

1. A composition for a lipstick sealant which forms a water-insoluble, transparent, flexible film preventing the transfer of lipstick to objects coming into contact with the lips, comprising at least 5% by weight of ethyl cellulose, no more than 4% by weight of essentials oils, the balance being ethanol, and wherein the substitution of ethoxyl groups is from 2.41 to 2.51 per anhydroglucose unit.

2. The composition of claim 1 wherein the concentration of ethyl cellulose is 6%–8% by weight.

3. The composition of claim 1 wherein the ethyl cellulose has an ethoxyl content of from 48% to 49.5% by weight.

4. The composition of claim 1 wherein the ethyl cellulose has a viscosity, as determined by ASTM D-319, of 8–11 centipoises when measured at 25 degrees C.

5. A lipstick sealant in accordance with claim 1,

6. The composition of claim 1 wherein the essential oils include coconut oil and vanilla oil.

7. The composition of claim 1 wherein the essential oils include bergamot oil and lavender oil.

8. The composition of claim 1 wherein the ethanol is 200 proof anhydrous ethanol.

* * * * *

UNITED STATES PATENT AND TRADEMARK OFFICE
CERTIFICATE OF CORRECTION

PATENT NO. : 5,462,737
DATED : October 31, 1995
INVENTOR(S) : D. Russell Pflueger It is certified that error appears in the above-indentified patent and that said Letters Patent is hereby corrected as shown below:

Title page, item [19], inventor: should read--Pflueger--.

Title page, item [76], inventor: should read-- D. Russell Pflueger--.

Signed and Sealed this

Thirtieth Day of January, 1996

Attest:

BRUCE LEHMAN

Attesting Officer     Commissioner of Patents and Trademarks